(12) United States Patent
Nunez et al.

(10) Patent No.: US 9,812,246 B1
(45) Date of Patent: Nov. 7, 2017

(54) APPARATUS AND METHOD FOR A COILED WIRE NEST AND FRAME FOR TOROIDAL INDUCTION

(71) Applicants: Daniel Nunez, Bronx, NY (US); Erica Lynn Nunez, Bronx, NY (US)

(72) Inventors: Daniel Nunez, Bronx, NY (US); Erica Lynn Nunez, Bronx, NY (US)

( * ) Notice: Subject to any disclaimer, the term of this patent is extended or adjusted under 35 U.S.C. 154(b) by 0 days.

(21) Appl. No.: 15/249,432

(22) Filed: Aug. 28, 2016

(51) Int. Cl.
| | |
|---|---|
| *H01F 27/28* | (2006.01) |
| *H01F 38/14* | (2006.01) |
| *H02K 11/00* | (2016.01) |
| *H01F 27/32* | (2006.01) |
| *H01F 41/071* | (2016.01) |

(Continued)

(52) U.S. Cl.
CPC ........... *H01F 27/2823* (2013.01); *A61N 2/02* (2013.01); *H01F 27/28* (2013.01); *H01F 27/29* (2013.01); *H01F 27/30* (2013.01); *H01F 27/323* (2013.01); *H01F 38/14* (2013.01); *H01F 41/071* (2016.01); *H02K 11/0094* (2013.01)

(58) Field of Classification Search
CPC ........................................... H01F 27/00–27/30
USPC ................. 336/65, 196, 198, 225, 229
See application file for complete search history.

(56) References Cited

U.S. PATENT DOCUMENTS 1,594,292 A * 7/1926 Zierick ................ H01F 17/02
140/71 R 1,614,151 A * 1/1927 Pfanstiehl ............... H01F 19/04
336/181

(Continued)

FOREIGN PATENT DOCUMENTS

| CA | 1236274 A | 5/1988 |
|---|---|---|
| CA | 1296511 C | 3/1992 |

(Continued)

*Primary Examiner* — Tuyen Nguyen
(74) *Attorney, Agent, or Firm* — PatNovo IP; Unisha Patel; Mohamed Azeez (57) ABSTRACT

Provided are claims and disclosure for a toroidal coil apparatus comprising a coiled wire nest further comprising: a top end layer disposed with a center through-layer; a circumferential side wall; a bottom end layer disposed with a center through-layer any one of a top end layer or bottom end layer radially extending through the circumferential side wall to form a vertically stacked coiled wire nest with a center through-nest, wherein the wire length and configuration of each stacked layer is identical and the distance between adjacent coiled wire is identical; at least a single or a plurality of inputs of at least two counter-directional channels in electrical communication with the coiled wire nest and at least a single or plurality of outputs of at least two counter-directional channels; and a coiled wire nest frame, further comprising: a latitudinal center hub with a plurality of slots; a vertical disc with a plurality of slots with staggered teeth; wherein the said vertical disc with staggered teeth is inserted into each slot of the said latitudinal center hub; the said staggered teeth are configured to shape a coiled wire nest with at least two stacked layers of wire with a crossed winding pattern, wherein the wire length and configuration of each stacked layer is identical and the distance between adjacent coiled wire is identical; and a vacuous center in communication with the center through layer of the top end layer and bottom end layer to shape the center through-nest of the coiled wire nest.

21 Claims, 8 Drawing Sheets

(51) Int. Cl.
*H01F 27/29* (2006.01)
*A61N 2/02* (2006.01)
*H01F 27/30* (2006.01)

(56) References Cited

U.S. PATENT DOCUMENTS

| | | | |
|---|---|---|---|
| 1,698,650 A * | 1/1929 | Parks | H01F 17/02 |
| | | | 29/605 |
| 1,718,826 A * | 6/1929 | Kuen | H01F 30/16 |
| | | | 29/605 |
| 2,763,441 A | 9/1956 | Frederick | |
| 2,865,573 A | 12/1958 | Tarara et al. | |
| 4,079,895 A | 3/1978 | de Fenffe | |
| 4,263,479 A | 4/1981 | Lange et al. | |
| 4,639,707 A * | 1/1987 | Tanaka | H01F 27/306 |
| | | | 336/185 |
| 4,724,603 A | 2/1988 | Blanpain et al. | |
| 4,868,534 A | 9/1989 | Pikul | |
| 4,878,291 A | 11/1989 | Suguri | |
| 5,021,738 A | 6/1991 | Vernon et al. | |
| 5,175,462 A | 12/1992 | Yoshino et al. | |
| 5,331,729 A | 7/1994 | Moorehead | |
| 5,507,442 A | 4/1996 | Konno et al. | |
| 5,583,475 A | 12/1996 | Raholijaona et al. | |
| 6,557,793 B2 | 5/2003 | Nakazawa et al. | |
| 6,990,729 B2 * | 1/2006 | Pleskach | H01F 17/0033 |
| | | | 156/250 |
| 8,416,050 B2 * | 4/2013 | Mino | H01F 17/06 |
| | | | 336/147 |
| 2007/0279174 A1 * | 12/2007 | Buswell | H01F 27/25 |
| | | | 336/170 |
| 2008/0036463 A1 | 2/2008 | Hsieh et al. | |
| 2014/0070541 A1 | 3/2014 | Irvin, Sr. | |
| 2015/0011126 A1 | 1/2015 | Zhou et al. | |
| 2015/0075670 A1 | 3/2015 | Bonanni et al. | |
| 2017/0040106 A1 | 2/2017 | Cobos Reyes et al. | |

FOREIGN PATENT DOCUMENTS

| | | |
|---|---|---|
| CN | 201204329 Y | 3/2009 |
| CN | 204143999 U | 2/2015 |
| EP | 0632472 A1 | 1/1995 |

* cited by examiner

APPARATUS AND METHOD FOR A COILED WIRE NEST AND FRAME FOR TOROIDAL INDUCTION

BACKGROUND

Field

The field of the invention relates to an apparatus and method for an inductor coil, and, more particularly an apparatus and method for toroidal induction, wherein the specific configuration and other characteristics of the frame and coil geometry contribute to increased electro-magnetism and inductance.

Related Art

Inductors are unresisting electronic components that store energy in the form of a magnetic field. Every individual conductor has a certain amount of inductance associated with it. In order to obtain higher values of inductance, the wire can be formed into a loop or coil. The amount of inductance attributable to a particular inductor device is generally proportional to the number of turns in the coil, the radius of the coil and the type of material around which the coil is wound.

For a particular inductor having a precise number of turns and a precise coil radius it is well known that an air core will result in the least inductance because it has a permeability of 1.0 (the terms permeability and permittivity as used herein should be understood to mean relative permeability and relative permittivity, respectively). Other types of dielectric core materials will behave similarly if they also have a relative permeability close to 1.0. Conversely, ferromagnetic materials, which have higher permeability values, are often used as core materials to increase the inductance achieved for a particular coil configuration. Iron powder or ferrite cores do not need the additional air gap since it is integrated into the material and, in consequence, spread within the complete core volume. This reduces the eddy current losses in the winding and the remaining eddy current losses are distributed throughout the winding length.

The main advantage of the toroidal shape lies in its symmetry where, the amount of magnetic flux that escapes outside the core (leakage flux) is low, therefore it is more efficient and thus, radiates less electromagnetic interference (EMI) which must be reduced to the levels defined by international standards to ensure that one equipment is able to work with other equipment. Because the toroid is a closed-loop core it will have a higher magnetic field and thus higher inductance and Q factor than an inductor of the same value with a straight core (solenoid coils). This is because most of the magnetic field is contained within the core. By comparison, with an inductor with a straight core, the magnetic field emerging from one end of the core have a long path through air to enter the other end. In addition, because the windings are relatively short a toroidal transformer will have a lower secondary impedance which will increase efficiency and electrical performance.

Toroid inductors are used in medical devices, telecommunications, musical instruments, industrial controls, refrigeration equipment, ballasts, electronic clutches, electronic brakes, in the aerospace & nuclear fields, in air conditioner equipment and in amplifiers. Other applications include noise filtering for switching regulators, power supplies, power amplifiers and train control circuits.

U.S. Pat. No. 6,990,729 B2 to Harris Corp., titled "Method for forming an inductor", suggests an inductor and a method for forming an inductor. The method includes forming in a ceramic substrate a first plurality of conductive vias radially spaced a first distance from a central axis so as to define an inner circumference. A second plurality of conductive vias is formed radially spaced a second distance about the central axis so as to define an outer circumference. A first plurality of conductive traces forming an electrical connection between substantially adjacent ones of the first and second plurality of conductive vias is formed in a first plane defined orthogonal to said central axis. The conductive vias and the conductive traces together define a three-dimensional toroidal coil. However, it fails to suggest the specific spacing between the adjacent vias is not identical thus, leading to no uniformity in the distance between the adjacent vias hence, a decrease in resonance.

A PCT Application number WO 2010004491 A1 to Rijck Alexander C. De titled, "Toroidal coil arrangement", discloses a first toroidal coil with a first set of windings which progress in a counterclockwise direction along the toroid, and a second set of toroidal coils with a second set of windings, wherein both toroid coils are electrically connected with each other. The coil arrangement in the PCT application is especially suitable for use as a part of an electronic circuit which is positioned within the examination volume of a magnetic resonance imaging system, because the net axial magnetic field of this coil arrangement is substantially reduced so that disturbing interferences with the functioning of the MM system, especially with the MR image generation, are accordingly decreased or prevented. However, the application fails to address a very important fact of the spacing as well as the distance between the coils, which leads to a lack of uniformity in resonance.

SUMMARY

These and other features and improvements of the present application will become apparent to one of ordinary skill in the art upon review of the following detailed description when taken in conjunction with the several drawings and the appended claims.

The present invention fills a void left behind by the current art by providing for an apparatus and method for manufacturing a coiled wire nest for increased induction. One object of the invention is to provide for an apparatus comprising a coiled wire nest for increased induction, further comprising a top end layer disposed with a center through-layer; a circumferential side wall; a bottom end layer disposed with a center through-layer any one of a top end layer or bottom end layer radially extending through the circumferential side wall to form a vertically stacked coiled wire nest with a center through-nest, wherein the wire length and configuration of each stacked layer is identical and the distance between adjacent coiled wire is identical; at least a single or a plurality of inputs of at least two counter-directional channels in electrical communication with the coiled wire nest and at least a single or plurality of outputs of at least two counter-directional channels.

Yet in another exemplary objective of the invention, a coiled wire nest frame may be provided, further comprising a latitudinal center hub with a plurality of slots; a vertical disc with a plurality of slots with staggered teeth; wherein the said vertical disc with staggered teeth is inserted into each slot of the said latitudinal center hub; the said staggered teeth are configured to shape a coiled wire nest with at least two stacked layers of wire with a crossed winding pattern, wherein the wire length and configuration of each stacked layer is identical and the distance between adjacent coiled wire is identical. The vacuous center in communication with the center through layer of the top end layer and bottom end layer to shape the center through-nest of the coiled wire nest. The slots and, or teeth allow for the coiled wire nest to achieve ideal spacing between wire coil. The even spacing in wire coil and stable progression of winding is absolutely critical for the apparatus to achieve a stable impedance/ resistance for circuit integration.

Another objective of the present invention is to provide a method of manufacturing the coiled wire nest and frame for increased induction. The method comprising inserting a vertical disc, each disc with slots with staggered teeth on the outer-most portion of the disc, into each slot of a latitudinal center hub, wherein each slot is on an outermost portion of the hub and surrounding a vacuous center; feeding a wire at a first slot of a first disc and then shifting position to any one of a preceding or proceeding slot of a proximal disc, such that when the entire length of the wire is fed into each teeth of every slot of all of the discs by winding in any one of a alternating clockwise/counter-clockwise, clockwise, counter-clockwise direction, the wire form a coiled wire nest with at least two stacked layers of wire with a crossed, diagonal winding pattern, wherein the wire length and configuration of each stacked layer is identical and the distance between adjacent coiled wire is identical; forming a center bore in communication with the center through layer of the top end layer and bottom end layer to shape a center through-nest of the coiled wire nest; and sanding and soldering the remaining terminal wire leads.

Still another objective of the present invention is to provide a toroidal coil operably coupled to an electro-magneto therapy apparatus, wherein the magnetic field generated interacts with the electro-magneto therapy apparatus to create a confined therapeutic pulse field. The electro-magneto therapy apparatus may be disposed with any one of, or combination of, a pressure, cortisol, lactate, bioimpedance, and, or a sensor for monitoring blood flow. The electro-magneto therapy apparatus may further comprise an interface means for transmitting the data from said sensor to a storage and, or processor means, over a network; and based on the said data and a user input data, provide any one of, or combination of, a health and wellness tracking function, user history function, network sharing function, and, or a personalized recommendation function. Other objects of the invention include providing for a health and wellness training program based on any one of, or combination of, the health and wellness tracking function, user history function, network sharing function, and personalized recommendation function.

Other devices, apparatus, and/or products according to embodiments will be or will become apparent to one of ordinary skill in the art upon review of the following drawings and further description. It is intended that all such additional devices, apparatus, and/or products be included within this description, be within the scope of the present invention, and be protected by the accompanying claims. Furthermore, additional aspects and advantages of this invention may be realized in other applications, aside from the intended application of increasing induction. Other pertinent applications that may exploit the aspects and advantages of this invention are: electro-magnetic therapy/rehabilitation, wireless charging, acoustic amplification, vehicular power-train control and management—each apparatus-agnostic or commercially paired.

BRIEF DESCRIPTION OF THE DRAWINGS

The drawings illustrate the design and utility of embodiments of the present invention, in which similar elements are referred to by common reference numerals. In order to better appreciate the advantages and objects of the embodiments of the present invention, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which.

DETAILED DESCRIPTION

In the following description, for purposes of explanation, numerous specific details are set forth in order to provide a thorough understanding of the invention. It will be apparent, however, to one skilled in the art that the invention can be practiced without these specific details.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but, not other embodiments.

Figure 1A:
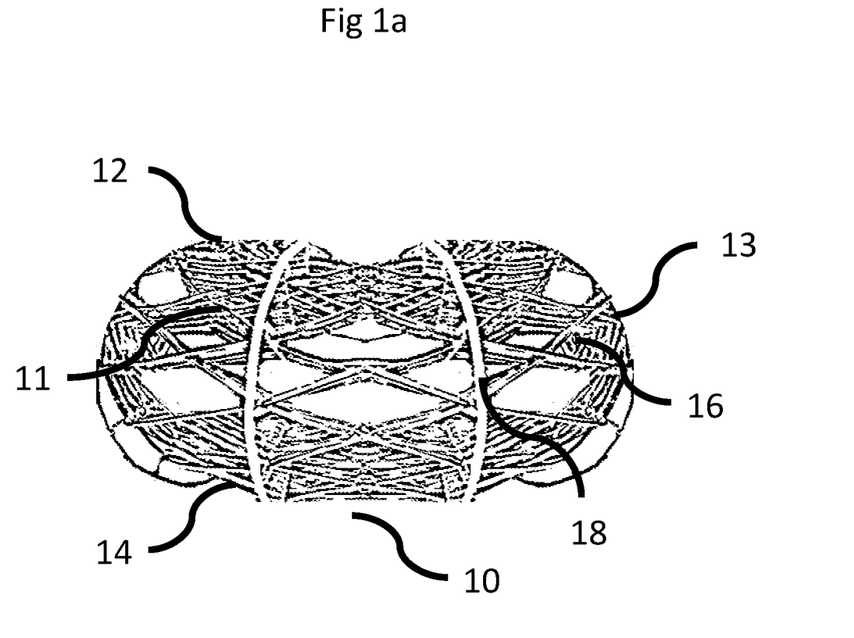
FIG. 1a is a front elevational view diagram of an apparatus in accordance with an aspect of the invention.

Now in reference to FIG. 1a, this depicts the toroidal coil apparatus for increased induction in accordance with an aspect of the invention. In a preferred embodiment, the toroidal coil apparatus 10 comprises: a coiled wire nest 11 further comprising: a top end layer 12 disposed with a center through-layer; a circumferential side wall 13; a bottom end layer 14 disposed with a center through-layer any one of a top end layer 12 or bottom end layer 14 radially extending through the circumferential side wall 13 to form a vertically stacked coiled wire nest 11 with a center through-nest 15, wherein the wire length and configuration of each stacked layer is identical and the distance between adjacent coiled wire is identical; at least a single or a plurality of inputs of at least two counter-directional channels in electrical communication with the coiled wire nest 11 and at least a single or plurality of outputs of at least two counter-directional channels; and a coiled wire nest frame 16, further comprising: a latitudinal center hub 17 with a plurality of slots; a vertical disc 18 with a plurality of slots 19a with staggered teeth 19*b*; wherein the said vertical disc 18 with staggered teeth 19*b* is inserted into each slot of the said latitudinal center hub 17; the said staggered teeth 19*b* are configured to shape a coiled wire nest 11 with at least two stacked layers of wire with a crossed winding pattern, wherein the wire length and configuration of each stacked layer is identical and the distance between adjacent coiled wire is identical; and a vacuous center in communication with the center through layer of the top end layer 12 and bottom end layer 14 to shape the center through-nest 15 of the coiled wire nest 11.

Figure 1B:
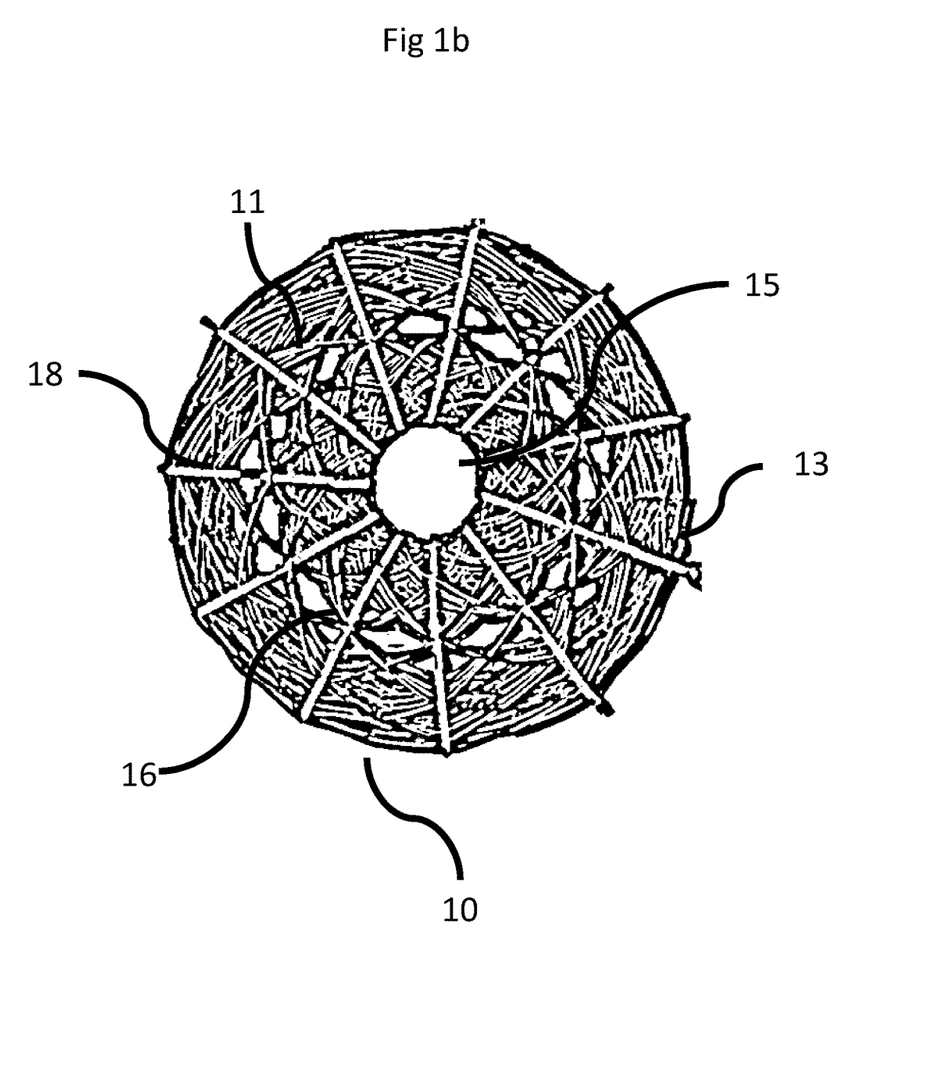
FIG. 1b is a top plan view diagram of the apparatus in accordance with an aspect of the invention.

In a preferred embodiment, as FIG. 1*b* shows, the coiled wire nest 11 may be comprised of a solid wire, which is circular, having standard ductile and tension values. It may be comprised of any one of, or combination of, copper, bronze, brass, iron, aluminum, platinum, gold, silver, and related alloys. Additionally, it may be further plated with silver, tin, and, or nickel. Alternatively, a multi-strand bundled wire may be used for the wire coil nest 11, and the wire may take on alternative dimensions, such as square, hexagonal, flattened, and, or rectangular. Wire properties may vary, such as gauge, Tensile strength, ductility, creep resistance, corrosion resistance, coefficient of thermal expansion, thermal conductivity, and, or solderability.

Figure 1C:
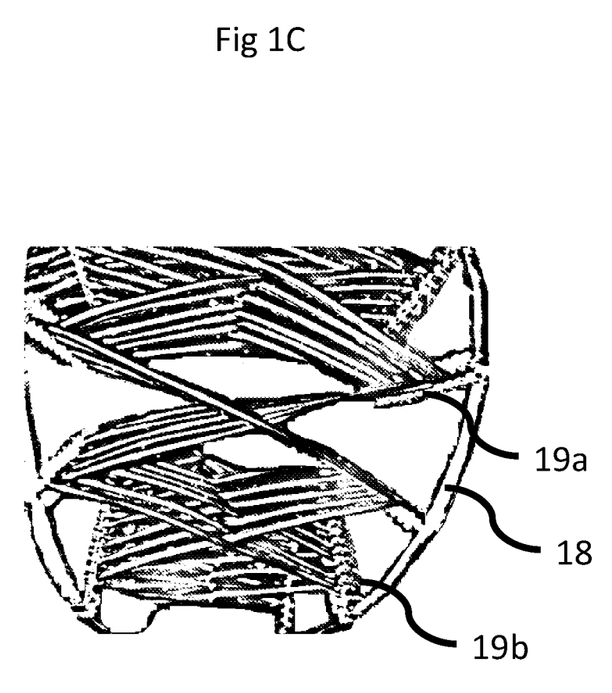
FIG. 1c is a fragmentary sectional view diagram of the apparatus in accordance with an aspect of the invention.

In a preferred embodiment, as shown in FIG. 1*c*, slots 19*a* and, or teeth 19*b* allow for the coiled wire nest to achieve ideal spacing between wire coil. The even spacing in wire coil and stable progression of winding is absolutely critical for the apparatus to achieve a stable impedance/resistance for circuit integration. Additionally, the even spacing of the wire coil and the specific configuration of the winding pattern are conducive to a stable resonance and energy amplification/transference. Alternatively, the latitudinal center hub may have less than 11 slots for vertical discs 18, or more than 11 slots. Each vertical disc 18, alternatively, may have thin slots 19*a* that are empty (lack the teeth 19*b*). In such an empty slot configuration, while spacing between wire coil may be achieved, spacing may not be even without the teeth. The number of slots 19*a* may vary, wherein vertical discs 18 with a greater number of slots 19*a* results in a denser wire coil nest. Vertical discs with fewer slots 19*a* result in a less dense wire coil nest 10. Density of wire coil nest may be directly correlated with inductance, impedance, resistance, and any other electrical parameter and, or outcome. The slots 19*a* may exhibit teeth 19*b*, which may be configured in any one of, or combination of, staggered, staggered with increased spacing, aligned, and, or aligned with increased spacing.

In alternative embodiments, an insulation layer interposed between the wires may be provided for maximizing spacing while still achieving an optimal coil wire density of the overall nest. In such a configuration, slots 19*a* without teeth may be chosen since spacing will be guaranteed by the interposed insulation. Any one of insulating material with lower capacitance (pf/ft), lower attenuation, and a lower dielectric constant (Er) may be chosen, from solids, foam, and, or semi-solids. Examples include halogen, non-halogen, thermoplastic, PVC, polyethylene, polyurethane, polypropylene, silicone rubber, FEP, Tefzel, Neoprene, and, or Hypalone.

In yet other alternative embodiments, a base (not shown) may be surrounded by a sealing lip, which forms a secure contact point with any one of a flat horizontal, flat vertical, or un-flat surfaces. The sealing lip may have a beveled outer edge, or a brim. The size and axial tilt of the bevel may vary depending on the purpose of the use. For instance, the size of the bevel and degree of the axial tilt may be larger for larger toroidal coils; smaller for smaller coils. Alternatively, coils intended for un-flat surface areas or vertical surfaces may have the larger bevel size and higher degree of axial tilt; smaller for more flat and horizontal surfaces.

Still in reference to the sealing lip, the lip may be composed of any one of, a rubber silicon composition. Alternatively, any one of a highly pliable, thermoplastic polymer, which does not compromise the conductive properties of the coiled wire nest, while still being able to form a tight contact seal, may be used for the lip composition. Moreover, the sealing lip and the coiled wire nest may be a unitary, contiguous construction of any one of conductive material. There may be columnar extensions, protrusions, collapsible, or modular base/sealing lip elements.

The sealing lips composition, dimension, and design are configured to form a seal with a contact surface by using a negative pressure created within lip housing/base. A user may squeeze any one of, or combination, of the side wall and, or top end of the lip housing/base using any one of or a combination of mechanical force, electromechanical force exerted by the user. In yet another alternative embodiment, the negative pressure may be created by suctioning the air within the lip housing/base by user inhalation, or by any other suctioning means. In other embodiments, the coiled wire nest may be coupled to a base void of any sealing lip, wherein there is no secure contact point, and the coiled wire nest simply rests on a surface. In yet other embodiments, the coiled wire nest may not be coupled to either a base, nor a base with a sealing lip, and instead, simply rest on a surface via the bottom end layer.

Figure 2:
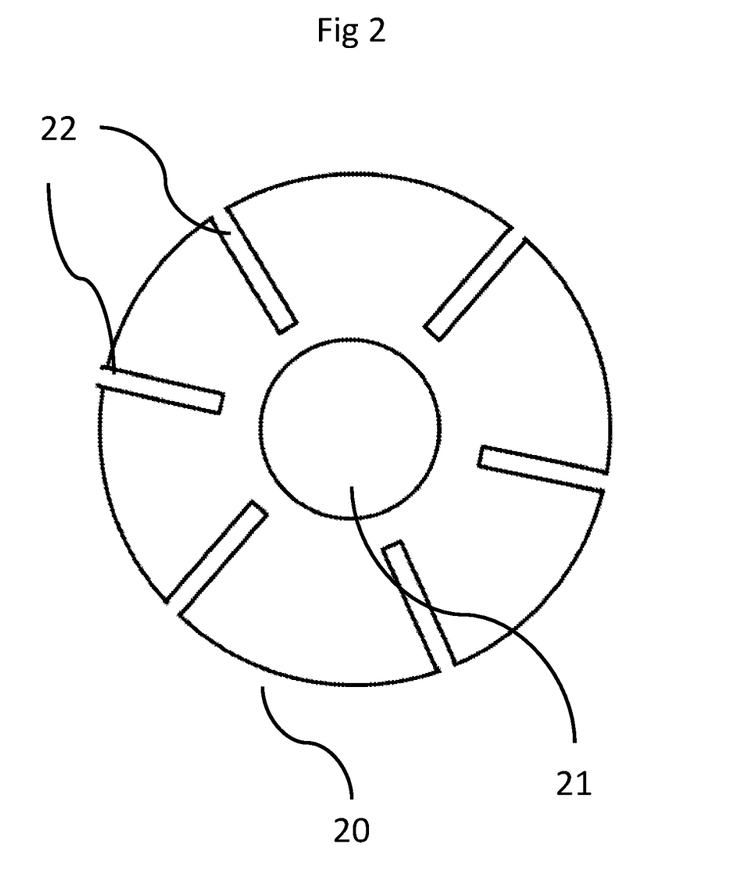
FIG. 2 is a top plan view diagram of the apparatus in accordance with an aspect of the invention.

Now in reference to FIG. 2, this depicts the coiled wire nest frame 20 for increased induction in accordance with an aspect of the invention. In a preferred embodiment of the present invention, a coiled wire nest frame 20, further comprises of a latitudinal center hub 21 with a plurality of slots 22, a vertical disc 23 with a plurality of slots 24 with staggered teeth 25, wherein the said vertical disc 23 with staggered teeth 25 are inserted into each slot 22 of the said latitudinal center hub 21.

Furthermore, in a preferred embodiment of the present invention, the said staggered teeth 25 are configured to shape a coiled wire nest 26 with at least two stacked layers of wire with a crossed winding pattern, wherein the wire length and configuration of each stacked layer is identical and the distance between adjacent coiled wire is identical. Additionally, in another preferred embodiment of the invention, a vacuous center is in communication with the center through layer of the top end layer and bottom end layer to shape the center through-nest of the coiled wire nest 11.

Further yet, in another preferred embodiment of the invention, the coiled wire nest 26 comprises of at least two toroidal coils stacked in series. Additionally, in another preferred embodiment, the coiled wire nest 26 further comprises of, at least a single or a plurality of inputs of at least two counter-directional channels, each channel with a multiple of 12 wires, in electrical communication with the coiled wire nest 26 and at least a single or plurality of outputs of at least two counter-directional channels.

In another preferred embodiment of the present invention the coiled wire nest 26 may further comprise of any one of a size gauge wire for coiling into the toroid and may be any one of or combination, but not limited to, of a conducting material, such as enameled wire, iron, ferrite, copper, and, or high-voltage insulator wire.

In an alternative embodiment of the invention, a coiled wire nest frame 20 may comprise of a latitudinal center hub 21 with a plurality of slots 22, which may be permanently attached to a vertical disc 23 with a plurality of slots 24 and staggered teeth 25. Alternatively, the latitudinal center hub 21 may be removably attached to a vertical disc 23 with a plurality of staggered teeth 25 and or may be sealed with a beveled lip sealant, which forms a secure contact point with any one of a flat horizontal, flat vertical, or un-flat surfaces. The sealing lip may have a beveled outer edge, or a brim. The size and axial tilt of the bevel may vary depending on the purpose of the use. Additionally, the vertical disc 23 may comprise of any one of, or a combination of an odd or even number of the staggered teeth 25.

Figure 3A:
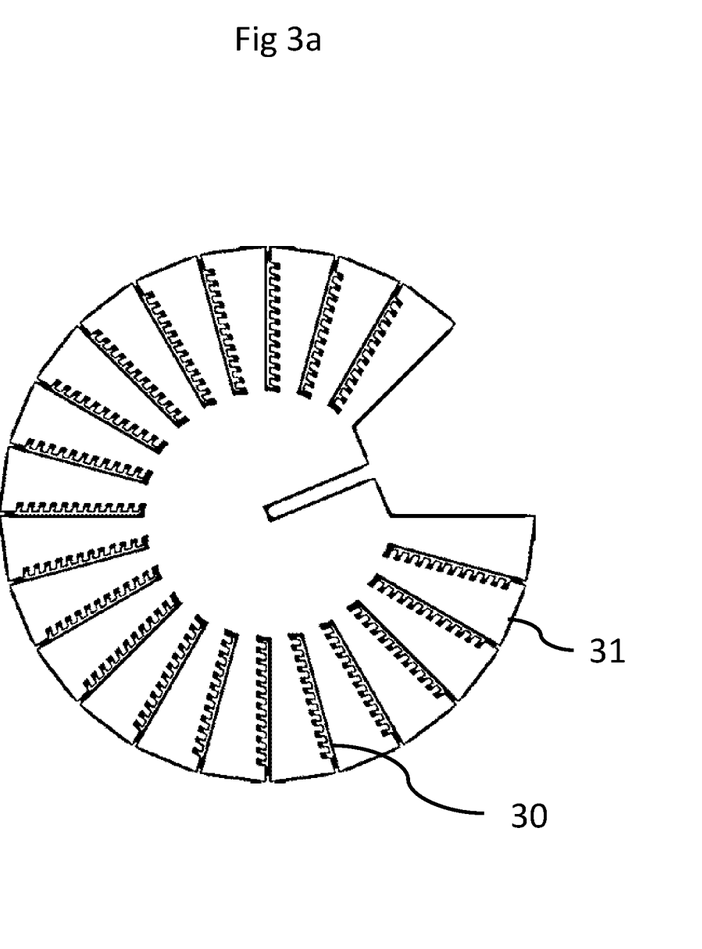
FIG. 3a is a top plan view diagram of the apparatus in accordance with an aspect of the invention.

FIG. 3a depicts a top view of the vertical disc in accordance to an aspect of the invention. As shown in FIG. 3a, in a preferred embodiment of the invention, a plurality of the staggered teeth 30 on the vertical disc 31 are configured to shape a coiled wire nest with at least two stacked layers of wire with a crossed winding pattern, wherein the wire length and configuration of each stacked layer is identical and the distance between adjacent coiled wire is identical.

Additionally, in yet another preferred embodiment of the invention, the distance between the each of staggered teeth 30 on the vertical disc 31 may be equidistant to maintain a uniform distance between the wires when configured to shape a coiled wire nest.

Further yet, in another alternative embodiment of the invention, the shape of the staggered teeth 30 may be any one of, or a combination of triangular, hooks, triangular-hooks, zipper-like, to maintain a uniform distance between the wires when configured to shape a coiled wire nest. Alternatively, in an embodiment of the invention, the staggered teeth 30 may be present on any one of, or a combination of, but not limited to, both the slot ends of the vertical disc 31.

In continuing reference to FIG. 3a, in another embodiment of the invention, the size of the staggered teeth 30 may vary depending on the size and the gauge of the wire used to configure a coiled wire nest. Further yet, in another alternative embodiment of the invention, the distance between each staggered teeth 30 on the vertical disc 31 may vary depending on the size and the gauge of the wire used to configure a coiled wire nest.

Additionally, in another alternative embodiment of the present invention, the vertical disc 31 with a plurality of slots with staggered teeth 30 may be any one of a highly pliable, thermoplastic polymer, which does not compromise the conductive properties of the coiled wire nest.

Figure 3B:
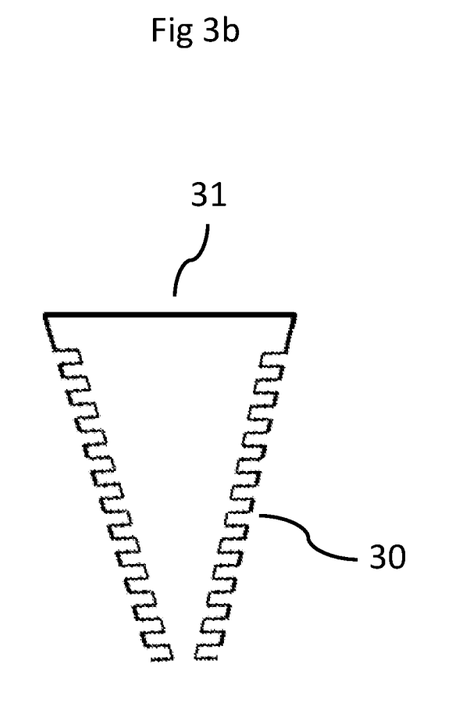
FIG. 3b is a fragmentary zoomed sectional view diagram of the apparatus in accordance with an aspect of the invention.

FIG. 3b depicts a fragmentary zoomed sectional view of the vertical disc 31 with staggered teeth 30 in accordance to an aspect of the invention. In a preferred embodiment of the invention, a plurality of the staggered teeth 30 on the vertical disc 31 are configured to shape a coiled wire nest with at least two stacked layers of wire with a crossed winding pattern, wherein the wire length and configuration of each stacked layer is identical and the distance between adjacent coiled wire is identical. Additionally, the slots on the vertical disc 31 with the staggered teeth 30 may be, any one of, or a combination of, but not limited to, varying sizes depending on the gauge size of the wires as well as the size of the staggered teeth 30. Further yet, in a preferred embodiment of the invention, there may be equal number of slots on the vertical disc 31. Alternatively, the number of slots on the vertical disc 31 may also vary.

In another preferred embodiment of the present invention, the number of vertical discs 31 with staggered teeth 30 slotted on the latitudinal center hub (not shown) may be of an even number. Alternatively, the number of vertical discs 31 slotted on the latitudinal center hub (not shown) may be of odd number and may be any one of, or a combination of, but not limited to, having equal number of staggered teeth or without staggered teeth. In yet another alternative embodiment, the slots of the vertical discs 31 may be void of any staggered teeth, while still achieving a uniform spacing between the wires with the exception of the crossing points dictated by the winding pattern. The spacing is key in achieving any one of, or a combination of, but not limited to stable impedance, resonance, resistance.

In yet another preferred embodiment of the present invention, the winding of the wires to configure a coiled wire nest is performed and described as follows. Once the framework of the vertical disc 31 with staggered teeth 30 is placed in the appropriate slots in the latitudinal center hub 21 (FIG. 2), the wire is placed along one of the slots along the center, outermost, position. In a preferred embodiment of the invention, the wire follows a trajectory that brings the wire in through the latitudinal center hub (not shown) creating the toroidal shape of the coiled wire nest. Further yet, a series of loops will miss each other till the final turn meets the wire at the starting point, which may be considered to be a single first layer of the coiled wire nest. In a preferred embodiment of the invention, the path of the wire of the first layer, may be in any one of, or a combination of, but not limited to, either in a clockwise or a counterclockwise direction to form a coiled wire nest.

Further yet, in a preferred embodiment of the invention, upon completion of the winding of the first layer, a second layer is wound atop the first layer in an opposing direction. In yet another preferred embodiment of the invention, a total of 12 'layers' of 14 AWG wire will complete the coiled wire nest. Additionally, after the completion of layers, the wire is trimmed, the terminals are sanded and soldered for future circuit integration thus, forming a center bore in communication with the center through layer of the top end layer (not shown) and bottom end layer (not shown) to shape a center through-nest of the coiled wire nest. In another embodiment of the invention, the coiled wired nest may be integrated with varying number of coiled wired nests to increase the scale of the apparatus for increased toroidal induction.

Alternatively, in another embodiment of the invention, the coiled wire nest may have varying number of layers as well as varying size of wires to form the coiled wire nest. Additionally, in another alternative embodiment of the invention, the winding of the second layer on the first layer may be, in any one of, or a combination of, but not limited to, the same or opposite direction. Further yet, each layer may also wound in any one of, or a combination of, but not limited to, in the same or opposite direction to form an entirely clockwise or entirely counter-clockwise coil. Alternatively, in another embodiment of the invention, a finer gauge wire may be incorporated and more layers may be added to produce a coil with a denser magnetic field.

Figure 4:
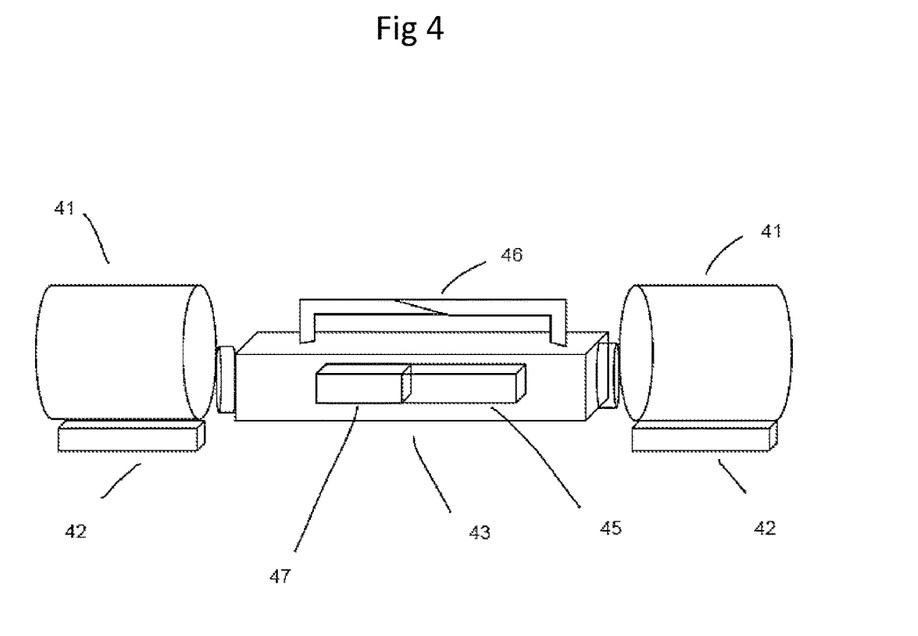
FIG. 4 is a block diagram of the apparatus in accordance with an aspect of the invention.

As shown in FIG. 4, the coiled wire nest 41 may be operably coupled to an electro-magneto therapy apparatus 43, wherein the magnetic field generated interacts with the electro-magneto therapy apparatus 43 to create a confined therapeutic pulse field. In such an apparatus, embedded within any one of or combination of, the coiled wire nest 41, coiled wire nest base 42, and, or electro-magneto therapy apparatus 43, may be a pressure, cortisol, lactate, and, or bioimpedance sensor 44. In further detail, at least one embedded sensor 44 for capturing a physiological data input from a user is provided. Additionally, an interface means for transmitting the data from the sensor to a storage and, or processor means, over a network. Finally, based on the said data, provide any one of, or combination of, a health tracking function, user history function, network sharing function, and personalized recommendation function. For instance, a user may input certain physical, physiological, pathological, environmental, and, or contextual parameters, which may layer onto already existing contextual data and accruing real-time sensor data, to provide richer and contextualized health and wellness recommendations. The embedded sensor 44 may be any one of, or combination of, a gyroscopic sensor, an accelerometer sensor, pressure, cortisol sensor, electrical impulse, respiration, bioimpedance, optical, and, or lactate sensor. In other embodiments, a suite of sensors may be provided that also real-time monitor physiological parameters, such as respiration rate, heart rate, cortisol levels. Bioimpedance sensors may be fitted onto any one of, or combination of, coiled wire nest 41, coiled wire nest base 42, and, or electro-magneto therapy apparatus 43, wherein an electrical-magnetic impulse is directed onto a user and differences in electrical potential represent the raw data for processing the above physiological parameters.

Embodiments may include the addition of a remote server to provide for back-end functionality and support. The server may be situated adjacent or remotely from the system and connected to each system via a communication network. In one embodiment, the server may be used to support verification or authentication of a user and a mobile device application function. In authenticating a user, a server may be further caused to recognize the user device at a particular system component, or any other system component that may be able to house a unique short-range communication tag. The server may identify and authenticate the particular component and user device by recognizing the unique tag, and then, authenticate the user by identifying the user device located at the particular component. The unique, short-range tag may be a NFC tag, RFID chip, Bluetooth, ZigBee, or any short-range communication protocol standard. The remote server may be further configured to support a user history function; a network sharing function; and support a health and wellness search engine. The remote server may be further configured to provide a user-control system, which authenticates the user and retrieves usage data of the user and applies the data against a predefined criterion of use.

Other embodiments may include a remote server that is configured to provide a contextually-aware suggestion engine, which may access the user history function and at least one user contextual information to cause the processor to display a suggested output on at least one display interface. Provisioning of the remote server may be delivered as a cloud service. In yet other embodiments, the coiled wire nest 41 operably coupled to the electro-magneto therapy apparatus 43 may be associated with an Internet of Things, whereby the apparatus is fully integrated into a user's home/gym/facility automation system, thereby providing additional contextual information for a contextually-aware health and wellness suggestion engine.

In continuing reference to FIG. 4, the electro-magneto therapy apparatus 43 may be disposed within a housing unit 45. The housing unit 45 may further be coupled to any one of, or combination of, extensions, grips, handles, spherical objects tethered/untethered 46, which interact with a user for therapeutic delivery to a skin surface and underlying tissue. Therapeutic pulses may be delivered in continuous fashion or in a discreet fashion. A control circuit 47 may be disposed within the housing unit 45 to further control the intensity and frequency of the therapeutic pulses. In other embodiments (not shown), the electro-magneto therapy apparatus may not be disposed within a specific housing unit, and may instead, be represented directly by any one of, or combination of, the extensions, grips, handles, spherical objects tethered/untethered. The electro-magneto therapy being delivered to the user directly from any one of, or combination of, the extensions, grips, handles, spherical objects tethered/untethered. The control circuit may be disposed within any one of the base of the wired coil nest, extensions, grips, handles, spherical objects tethered/untethered, stand-alone device and, or any of the combinations.

In other embodiments, two or more coiled wire nests 41 in a vertical orientation may be provided, wherein the electro-magnetic therapy apparatus 43 may be disposed between. The apparatus 43 may have two terminal end, wherein each end is disposed within the bore or center through-nest of the vertically oriented coiled wire nest 41. In some embodiments, the apparatus 43 may be a plasma tube. The plasma tube may be situated in the middle of two coiled wire nests 41 in a vertical orientation, wherein each terminal end of the plasma tube may be disposed within the bore or center through-nest of the vertically oriented coiled wire nest 41. Excitation of the gases by the electro-magnetic field created is evident by the turn of color of the tube. The coiled wire nest 41 may be scaled to fit a smaller form factor of a consumer device or scaled up to fit the scale of a more industrial application.

While not shown in FIG. 4, one embodiment of a coiled wire nest coupled to an apparatus may include the toroidal coil integrated as part of an electronic unit, whereby said electronic unit is powered by the toroidal coil. The coiled wire nest 41 may be scaled to fit a smaller form factor of a consumer device or scaled up to fit the scale of a more industrial application. The electronic unit may further be coupled to a device requiring powering or actuation. For instance, the electronic unit may be coupled to a motor further comprising a rotor unit and a stator unit. The electronic unit may also be step-up or step-down transformer or may be a AC/DC converter.

In other embodiments of coiled wire nests coupled to an apparatus, an axial assembly having a first end adapted to the toroidal coil for rotation about its longitudinal axis and an opposable end for mechanical actuation, may be provided. Other power distribution schemes may include at least one coiled wire nest interposed between any one of a battery, capacitor, fuel cell stack and a power distribution unit as part of a powertrain of any one of an automobile, bus, truck, marine vessel.

In yet other embodiments, the coupled apparatus may be any one of magnetic members and, or plate-like insulators interposed between an adjacent planar layer of toroidal coils. In other embodiments, the coiled wire nest may be integrated as part of a fixed structure, whereby any one of user devices within the confines of the fixed structure may be wirelessly powered by the coiled wire nest. Some embodiments may include a rectifier coupled to the coiled wire nest and the powered device, wherein the rectifier converts the electro/magnetic field into AC/DC voltage for powering the powered device. Examples of fixed structure are router-like devices, gateways, embedded within the structure of a dwelling or building, and, or situated in a public venue. The electro/magnetic field generated and, or amplified may be used for facilitating short-range and wide-area data transmission, as well. Still in continuing reference to the various apparatus coupled to a coiled wire nest, one embodiment may include at least one nest coupled to an acoustical apparatus. The acoustical apparatus may be in the form of any one of, or combination of, an input, and, or output.

Figure 5:
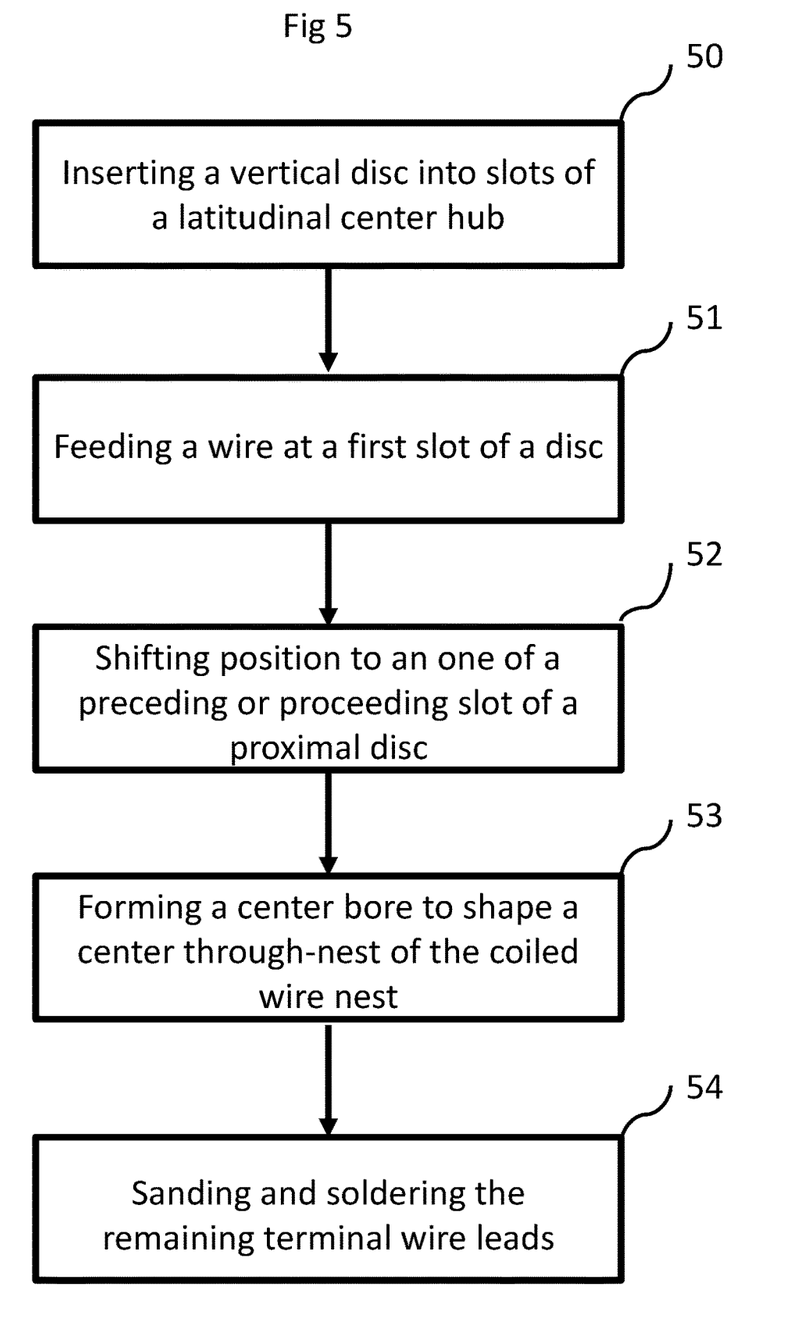
FIG. 5 is a flow diagram of the method in accordance with an aspect of the invention.

FIG. 5 describes a method of winding the wire coil onto the framework of the vertical disc and the latitudinal center hub. The steps involved in the method of winding the wire coil onto the framework is as follows: (1) inserting a vertical disc, each disc with slots with staggered teeth on the outermost portion of the disc, into each slot of a latitudinal center hub, wherein each slot is on an outermost portion of the hub and surrounding a vacuous center 50, (2) feeding a wire at a first slot of a first disc 51, (3) shifting position to any one of a preceding or proceeding slot of a proximal disc 52, such that when the entire length of the wire is fed into each teeth of every slot of all of the discs by winding in any one of an alternating clockwise/counter-clockwise, clockwise, counter-clockwise direction, the wire form a coiled wire nest with at least two stacked layers of wire with a crossed, diagonal winding pattern, wherein the wire length and configuration of each stacked layer is identical and the distance between adjacent coiled wire is identical, (4) forming a center bore in communication with the center through layer of the top end layer and bottom end layer to shape a center through-nest of the coiled wire nest 53, and (5) sanding and soldering the remaining terminal wire leads 54.

Alternatively, 3D printing technology may also be a viable and an affordable alternative in forming the framework of the vertical discs along with the latitudinal center hub however, it is recognized that many other different methods or variations of the described method could also be used.

The steps involved in 3D printing technology may be comprised of: (1) producing a 3-D model using computer-aided design (CAD) software, (2) convert the CAD drawing to the STL (standard tessellation language) format, (3) transfer to AM machine and STL file manipulation thereby designating the size and orientation for printing, (4) preparing the machine for a new print job including, but not limited to, refilling polymers, binders, tray to serve as a foundation and other consumables for the printer use, (5) building the prototype, (6) removing the printed object from the printer and (7) post-processing the printed object including, but not limited to, brushing off any remaining powder or bathing the printed object to remove water-soluble supports.

While this specification contains many specific execution details, these should not be interpreted as limitations on the scope of any inventions or of what may be claimed, but rather as descriptions of features specific to particular embodiments of particular inventions. Certain features that are described in this specification in the context of separate embodiments can also be implemented in combination in a single embodiment. Contrariwise, various features that are described in the context of a single embodiment can also be implemented and interpreted in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:

1. A toroidal coil apparatus comprising:
    a coiled wire nest further comprising:
        a top end layer disposed with a center through-layer;
        a circumferential side wall;
        a bottom end layer disposed with a center through-layer;
        any one of a top end layer or bottom end layer radially extending through the circumferential side wall to form a vertically stacked coiled wire nest with a center through-nest, wherein the wire length and configuration of each stacked layer is identical and the distance between adjacent coiled wire is identical;
    at least a single or a plurality of inputs of at least two counter-directional channels in electrical communication with the coiled wire nest and at least a single or plurality of outputs of at least two counter-directional channels; and
    a coiled wire nest frame, further comprising:
        a latitudinal center hub with a plurality of slots;
        a vertical disc with a plurality of slots with staggered teeth;
            wherein the said vertical disc with staggered teeth is inserted into each slot of the said latitudinal center hub;
            the said staggered teeth are configured to shape a coiled wire nest with at least two stacked layers of wire with a crossed winding pattern, wherein the wire length and configuration of each stacked layer is identical and the distance between adjacent coiled wire is identical; and
        a vacuous center in communication with the center through layer of the top end layer and bottom end layer to shape the center through-nest of the coiled wire nest.

2. The apparatus of claim 1, further comprising at least two toroidal coils stacked in series.

3. The apparatus of claim 1, further comprising at least a single or a plurality of inputs of at least two counter-directional channels, each channel with a multiple of 12 wires, in electrical communication with the coiled wire nest and at least a single or plurality of outputs of at least two counter-directional channels.

4. The apparatus of claim 1, further comprising any one of a size gauge wire for coiling into the toroid.

5. The apparatus of claim 1, further comprising any one of or combination of conducting material, such as enameled wire, iron, ferrite, copper, and, or high-voltage insulator wire.

6. The apparatus of claim 1, further comprising the toroidal coil with any one of varying size, varying input, and, or varying output.

7. The apparatus of claim 1, further comprising an additional conductive layer disposed on the core wall of the toroidal coil composed of any one of, or combination of, iron and, or ferrite.

8. The apparatus of claim 1, further comprising the toroidal coil operably coupled to an electro-magneto therapy apparatus, wherein the magnetic field generated interacts with the electro-magneto therapy apparatus to create a confined therapeutic pulse field.

9. The device of claim 8, wherein the electro-magneto therapy apparatus is disposed with any one of, or combination of, a pressure, cortisol, lactate, bioimpedance, and, or a sensor for monitoring blood flow.

10. The device of claim 8, further comprising:
    at least one embedded sensor for capturing a physiological data input;
    an interface means for transmitting the data from said sensor to a storage and, or processor means, over a network; and
    based on the said data and a user input data, provide any one of, or combination of, a health and wellness tracking function, user history function, network sharing function, and, or a personalized recommendation function.

11. The device of claim 8, wherein a health and wellness training program is based on any one of, or combination of, the health and wellness tracking function, user history function, network sharing function, and personalized recommendation function from any one of, or combination of, a sensor data input and, or user data input.

12. The apparatus of claim 1, further comprising the toroidal coil integrated as part of an electronic unit, whereby said electronic unit is powered by the toroidal coil.

13. The apparatus of claim 1, further comprising the toroidal coil integrated as part of a fixed structure, whereby any one of user devices within the confines of the fixed structure may be wirelessly powered by the toroidal coil.

14. The apparatus of claim 1, further comprising an axial assembly having a first end adapted to the toroidal coil for rotation about its longitudinal axis and an opposable end for mechanical actuation.

15. The apparatus of claim 1, further comprising the toroidal coil installed in a housing and coupled to a motor further comprising a rotor unit and a stator unit.

16. The apparatus of claim 1, further comprising the toroidal coil interposed between any one of a battery, capacitor, fuel cell stack and a power distribution unit as part of a powertrain of any one of an automobile, bus, truck, marine vessel.

17. The apparatus of claim 1, further comprising any one of magnetic members and, or plate-like insulators interposed between an adjacent planar layer of toroidal coils.

18. The apparatus of claim 1, further comprising the toroidal coil coupled to an acoustical apparatus.

19. A toroidal coil apparatus comprising:
    a coiled wire nest further comprising:
        a top end layer disposed with a center through-layer;
        a circumferential side wall;
        a bottom end layer disposed with a center through-layer
        any one of a top end layer or bottom end layer radially extending through the circumferential side wall to form a vertically stacked coiled wire nest with a center through-nest; and
    a coiled wire nest frame, further comprising:
        a latitudinal center hub with a plurality of slots;
        a vertical disc with a plurality of slots;
        wherein the said vertical disc is inserted into each slot of the said latitudinal center hub;
            the said vertical disc with the plurality of slots configured to shape a coiled wire nest with at least two stacked layers of wire with a crossed winding pattern, wherein the wire length and configuration of each stacked layer is identical and further having spacing between the wires except for wire crossing points in the crossed winding pattern; and
        a vacuous center in communication with the center through layer of the top end layer and bottom end layer to shape the center through-nest of the coiled wire nest.

20. The toroidal coil apparatus of claim 19, further comprising:
    any one of, or combination of, a base, and, or a sealing lip enveloping the base.

21. A method of manufacturing a coiled wired nest, the method comprising the steps of:
    inserting a vertical disc, each disc with slots with staggered teeth on the outermost portion of the disc, into each slot of a latitudinal center hub, wherein each slot is on an outermost portion of the hub and surrounding a vacuous center;
    feeding a wire at a first slot of a first disc and then shifting position to any one of a preceding or proceeding slot of a proximal disc, such that when the entire length of the wire is fed into each teeth of every slot of all of the discs by winding in any one of a alternating clockwise/counter-clockwise, clockwise, counter-clockwise direction, the wire form a coiled wire nest with at least two stacked layers of wire with a crossed, diagonal winding pattern, wherein the wire length and configuration of each stacked layer is identical and the distance between adjacent coiled wire is identical;
    forming a center bore in communication with the center through layer of the top end layer and bottom end layer to shape a center through-nest of the coiled wire nest; and
    sanding and soldering the remaining terminal wire leads.

* * * * *